United States Patent [19]

Kita

[11] 4,155,812

[45] May 22, 1979

[54] FERMENTATION PROCESS FOR CONVERTING L-GULONIC ACID TO 2-KETO-L-GULONIC ACID

[75] Inventor: Donald A. Kita, Essex, Conn.

[73] Assignee: Pfizer Inc., New York, N.Y.

[21] Appl. No.: 855,944

[22] Filed: Nov. 30, 1977

[51] Int. Cl.$^2$ ............................................. C12D 1/02
[52] U.S. Cl. ................................................. 195/30
[58] Field of Search ......................................... 195/30

[56] References Cited

U.S. PATENT DOCUMENTS 2,917,435   12/1959   Perlman ................................. 195/30

Primary Examiner—Alvin E. Tanenholtz
Attorney, Agent, or Firm—Connolly and Hutz

[57] ABSTRACT

L-gulonic acid as the calcium or sodium salt is converted to 2-keto-L-gulonate in high yield by means of a growing culture of selected strains of species of the genus Xanthomonas.

2 Claims, No Drawings

FERMENTATION PROCESS FOR CONVERTING L-GULONIC ACID TO 2-KETO-L-GULONIC ACID

BACKGROUND OF THE INVENTION 2-keto-L-gulonic acid is an important intermediate in vitamin C manufacture. Condensation of L-sorbose with acetone in the presence of sulfuric acid followed by oxidation with permanganate and hydrolysis of the diisopropylidene derivative by boiling yields 2 keto-L-gulonic acid as described in Helv. Chim. Acta., 17, 311 (1934) and U.S. Pat. No. 2,301,811. The preparation of 2-keto-L-gulonic acid by careful oxidation of L-sorbose with nitric acid is claimed in British Pat. No. 443,901 and Dutch Pat. No. 59,584. The selective reduction of 2,5-diketogluconic acid to yield a mixture of 2-ketogluconic acid and 2-ketogulonic acid is described in copending application, Ser. No. 749,509 filed Oct. 10, 1976.

SUMMARY OF THE INVENTION

This invention is concerned with the conversion of L-gulonic acid as the calcium or sodium salt to 2-keto-L-gulonate by means of a growing culture of selected strains of species of the genus Xanthomonas. Yields of 90% or greater are obtained with concentrations of L-gulonate up to 15%.

DETAILED DESCRIPTION OF THE INVENTION

A screening program was initiated for the selection of microorganisms capable of converting L-gulonate to 2-keto-L-gulonate. Microorganisms belonging to the genus Xanthomonas were selected from the varieties of microorganisms reported to be capable of oxidizing secondary alcohols to ketones.

A number of readily available, publicly held Xanthomonas cultures were individually transferred to test tubes each containing 10 ml of the following sterile aqueous culture medium:

| Ingredient | Grams/liter |
| --- | --- |
| Glycerol | 50.0 |
| Corn steep liquor | 5.0 |
| Dihydrogen ammonium phosphate | 1.0 |
| Dihydrogen potassium phosphate | 1.0 |
| Magnesium sulfate | 0.5 |
| Calcium L-gulonate | 10.0 |
| pH — 7.0 | |

The tubes were shaken on a rotary shaker for 3–5 days at 28° C. The broths were spotted on Whatman No. 1 and No. 4 paper and developed with a solvent system of methylethyl ketone:acetone:formic acid:water (80:6:2:12). 2-Keto-gulonic acid was located by spraying with a 0.2% o-phenylenediamine ethanolic solution containing 1% nitric acid. A yellow color develops on heating to about 70° C. High pressure liquid chromatography may also be used for identification.

Conversion of L-gulonate to 2-keto-L-gulonate was obtained by the following Xanthomonas cultures obtained from The American Type Culture Collection and The New Zealand Reference Culture Collection.

| | |
| --- | --- |
| Xanthomonas amaranthiocola | ATCC 11645 |
| begoniae | 8718 |
| " | 11725 |
| " | 11726 |
| campestris | 6402 |
| " | 13951 |
| holcicola | 13461 |
| incanae | 13462 |
| juglandis | 11329 |
| malvacearum | 9924 |
| " | 12131 |
| " | 12132 |
| " | 14981 |
| " | 14982 |
| " | 14983 |
| " | 14984 |
| " | 14985 |
| " | 14986 |
| melhusi | 11644 |
| papavericola | 14179 |
| Xanthomonas phaseoli | 11766 |
| " | 17915 |
| pruni | 15924 |
| translucens | 9000 |
| " | 9002 |
| " | 10731 |
| " | 10768 |
| " | 10769 |
| " | 10770 |
| " | 10771 |
| " | 10772 |
| begoniae | NZRRC 191-65 |
| | 193-62 |
| | 194-66 |
| | 75-65 |
| incanae | 574-63 |
| | 573-63 |
| campestris | 1686-65 |
| | 2385-68 |
| | 3984-74 |
| | 4013-74 |

The preferred microorganism is Xanthomonas translucens ATCC 10768 which quantitatively converts L-gulonate to 2-keto-L-gulonate.

In the practice of this invention, an aqueous nutrient medium containing an assimilable source of carbon and nitrogen is inoclated with a suitable L-gulonate converting strain of Xanthomonas. After aerobic propagation for about 24 to 48 hours at 24° to 34° C., preferably 28°–30° C., an aliquot is transferred to a fermentor containing an aqueous nutrient medium comprising a carbohydrate, an assimilable source of nitrogen and trace elements. Such media are, per se, well known to the art and may be selected from those described in the literature for the growth of Xanthomonas organisms.

The aqueous nutrient medium also contains about 8% (the solubility limit) of calcium gulonate. The sodium, potassium and ammonium salts of L-gulonic acid are inhibitory at this concentration to cell growth of the inoculum. One of these salts, preferably the sodium salt, is added at a level of 40 grams/liter of fermentation broth at the fermentation time of about 48 hours and an additional 30 grams/liter at about 72 hours. L-gulonic acid and L-gulono-1,4-lactone are not suitable conversion substrates for the production of 2-keto-L-gulonic acid. The calcium and sodium salts of L-gulonic acid are prepared from L-gulonic acid obtained by the hydrolysis of L-gulono-1,4-lactone which may be synthesized by the method described in Chem. Pharm. Bull., 13, 173 (1965) and Rec. Trav. Chim. des Pays-Bas, 74, 1365 (1955).

The conversion fermentation is conducted at a temperature of about 28°–30° C. with mechanical stirring at about 1700 r.p.m. and an aeration rate of about 0.75 volume of air per volume of broth per minutes. The optimum pH conversion range is fairly narrow (6.5 to 7.5). The fermentation is allowed to continue until a yield of at least 85% (based on L-gulonate) 2-keto-L-gulonate is obtained.

2-Keto-L-gulonate may be isolated and recovered as the free acid or in salt form by methods well known to those skilled in the art or hydrolyzing the 2-keto-L-gulonate in the fermentation broth to yield ascorbic acid.

EXAMPLE 1

A sterile aqueous inoculum medium of the following composition is prepared:

| Ingredient | Gram/liter |
| --- | --- |
| Urea | 2 |
| Corn steep liquor | 8 |
| Meat digest | 2 |
| Diammonium hydrogen phosphate | 2 |
| Dihydrogen potassium phosphate | 1 |
| Magnesium sulfate | 0.5 |
| pH — 6.5 | |

Cells of Xanthomonas translucens ATCC 10768 are transferred to shake flasks containing the above culture medium and shaken on a rotary shaker for about 24 hours at about 28° C.

An aliquot of the culture growth sufficient to provide a 5% inoculum is added to a 4-liter stirred fermentor containing 2 liters of the following production culture medium:

| Ingredient | Grams/liter |
| --- | --- |
| Corn steep liquor | 8 |
| Meat digest | 6 |
| Diammonium hydrogen phosphate | 1 |
| Dihydrogen potassium phosphate | 1 |
| Glucose | 10 |
| Calcium carbonate | 3 |
| Calcium L-gulonate | 80 |
| pH — 7.0 | |

The fermentation is conducted at a temperature of about 28°–30° C. with mechanical stirring at about 1700 r.p.m. and an aeration rate of about 0.75 volume of air per volume of broth per minutes. After a fermentation time of about 48 hours, 40 grams of sodium L-gulonate per liter of fermentation broth is added followed by an additional 30 grams per liter of fermentation broth at about 72 hours. The pH of the fermentation medium is controlled within the range of 6.5 to 7.5. The fermentation is continued until a yield of at least 85% (based on L-gulonate) 2-keto-L-gulonate is obtained.

EXAMPLE 2

The method of Example 1 may be repeated employing other Xanthomonas cultures capable of converting L-gulonate to 2-keto-L-gulonate.

What is claimed is:

1. A process for producing a mixture of the calcium with either the sodium or potassium or ammonium salt of 2-keto-L-gulonic acid which process comprises aerobically propagating, in an aqueous nutrient medium in the presence of a mixture of the calcium with either the sodium or potassium or ammonium salt of L-gulonic acid, a strain of a species of microorganism belonging to the genus Xanthomonas capable of converting said salts in said nutrient medium to the corresponding salts of 2-keto-L-gulonic acid.

2. The process of claim 1 wherein the Xanthomonas microorganism is Xanthomonas translucens ATCC 10768.

* * * * *